United States Patent [19]
Bethea

[11] Patent Number: 5,396,068
[45] Date of Patent: Mar. 7, 1995

[54] METHOD OF MAKING A SEMICONDUCTOR DEVICE INCLUDING INFRARED IMAGING, AND APPARATUS FOR USE IN THE IMAGING

[75] Inventor: Clyde G. Bethea, Plainfield, N.J.

[73] Assignee: AT&T Corp., Murray Hill, N.J.

[21] Appl. No.: 40,328

[22] Filed: Mar. 30, 1993

[51] Int. Cl.$^6$ ............................................. G01N 25/72
[52] U.S. Cl. .................................. 250/330; 250/332; 250/358.1; 374/5; 437/8
[58] Field of Search ............ 250/330, 332, 342, 358.1; 437/8; 374/4, 5, 137

[56] References Cited

U.S. PATENT DOCUMENTS

| | | | |
|---|---|---|---|
| 4,466,746 | 8/1984 | Hancock et al. | 374/5 |
| 5,294,198 | 3/1994 | Schlagheck | 250/332 |
| 5,302,830 | 4/1994 | Shivanandan | 250/332 |

OTHER PUBLICATIONS

Woolaway, "New Sensor Technology for the 3–5 μm Imaging Band", Photonics Spectra, Feb. 1991, pp. 113–119.

Masi, "What can Thermal Imaging Do For You", Test & Measurement World, May 1988.

Weight, "Thermography Testing of Production PC Boards", Electronic Packaging & Production, Oct. 1981, pp. 69–74.

"Imager Finds Microelectronic Hot Spots", by R. J. Stetson et al., Laser Focus World, Jun. 1990.

"Thermal Resistance of Heterostructure Lasers", by W. B. Joyce et al., Journal of Applied Physics, vol. 46, No. 2, Feb. 1975, pp. 855–862.

Primary Examiner—Carolyn E. Fields
Attorney, Agent, or Firm—Eugen E. Pacher

[57] ABSTRACT

The inventive methods of making a semiconductor device, e.g., a laser, comprise thermal (e.g., 3–5 μm wavelength) imaging of a powered, partially completed device. The thermal image is obtained with apparatus that is capable of forming a substantially diffraction-limited image on a sensor array with an acquisition time of no more than 0.1 seconds, preferable no more than 0.01 seconds. In preferred embodiments, the image has temperature resolution of 0.01° C. or better. Exemplary apparatus is disclosed. The inventive method facilitates, for instance, early identification of devices that are likely to fail lifetime requirements.

7 Claims, 2 Drawing Sheets

METHOD OF MAKING A SEMICONDUCTOR DEVICE INCLUDING INFRARED IMAGING, AND APPARATUS FOR USE IN THE IMAGING

FIELD OF THE INVENTION

This application relates to semiconductor device manufacture, exemplarily to manufacture of opto-electronic devices such as semiconductor lasers, and to infrared imaging apparatus that is adapted for use in semiconductor device manufacture.

BACKGROUND OF THE INVENTION

As is well known, semiconductor device manufacture typically involves a multiplicity of steps. Many (if not all) of the steps, if not carried out according to specification, can result in devices that do not pass final inspection, or that fall during life testing. It is obviously expensive, and thus highly undesirable, to have to substantially complete device manufacture and then to subject all, or at least a representative sample, of the devices to a life test in order to ascertain the adequacy of some intermediate manufacturing step. Thus, it would be highly desirable to have available an inspection technique that could be used, inter alia, to pre-screen devices, and to identify potentially unreliable devices. This application discloses such a technique, discloses a manufacturing process that comprises an inspection step that involves use of the technique, and also discloses apparatus that can be used to practice the technique.

Although the apparatus and technique are advantageously employed in semiconductor device manufacturing, theft use is not thus limited. In particular, the apparatus and technique can also advantageously be used in the development of new semiconductor device designs and/or of semiconductor device manufacturing methods, as those skilled in the art will recognize. It can also be used to test packaged devices.

Thermal imaging of semiconductor devices is known. See, for instance, R. J. Stetson, et al., *Laser Focus World*, June 1990. As stated in that article, non-contact temperature measurements can be made ". . . with a spatial resolution as small as 15 μm." The article further discloses that the prior art IR imaging method utilizes scanning, with the scanning rate being on the order of 45 microseconds/point.

These capabilities, although adequate for some purposes, are inadequate for other purposes. In particular, it would be desirable for many purposes (exemplarily including semiconductor laser fabrication) to have available thermal imaging means capable of providing a substantially diffraction-limited thermal image of a body (exemplarily in the approximate wavelength range 3–5 μm). It would also be deskable if the high resolution thermal imaging means could form an image at a given moment in time (i.e., provide a "snapshot" of the temperature distribution at a given moment in time). The former capability could, for instance, be used to pinpoint the location and cause of hot spots in semiconductor lasers, and to assess the uniformity of the heat sinking or of the laser, and the latter could be used to, e.g., reveal transient thermal states. This application discloses thermal imaging means that can provide these capabilities.

SUMMARY OF THE INVENTION

In a broad aspect the invention is embodied in a semiconductor manufacturing process that comprises an inspection step that involves energizing a (typically partially completed, but not excluding completed) device and determining the temperature distribution over the surface of the energized device. The temperature distribution is determined by forming a substantially diffraction-limited real time infrared (IR) image of the device by means that comprise a multi-pixel IR detector array. This invention is also embodied in apparatus for forming said IR image. In particular, it is embodied in IR-imaging apparatus that is capable of forming substantially diffraction-limited (e.g., 5 μm spatial resolution for radiation in the 3–5 μm wavelength range) thermal image substantially in real time (e.g., capable of acquisition time $\lesssim 10$ ms), with high (e.g., $\Delta T \lesssim 0.01°$ C.) temperature resolution.

More specifically, in an exemplary embodiment the manufacturing method comprises providing a semiconductor body, and forming on and/or in the body one or more semiconductor devices. A given device has a surface and comprises contact means such that an electrical current can be caused to flow through the device. The method further comprises causing, prior to completion of the device or devices, current to flow at least through the partially completed given device (e.g., through a laser chip that is bonded to a submount), forming an image of at least a portion of the partially completed given device, said image being an IR image comprising features that are representative of the temperature at a multiplicity of points (typically providing the temperature distribution) of the given partially completed device. The method still further comprises comparing the temperature corresponding to at least one of said features of the IR image to a predetermined target value, and carrying out at least one further processing step in accordance with the result of the comparing step. Exemplarily, the processing step is completion of device packaging if the comparison did not reveal unacceptable departure from the target, or rejection of the device if the comparison revealed unacceptable departure.

Significantly, the IR image is formed with imaging apparatus that is adapted for forming, with an acquisition time of no more than 0.1 (preferably no more than 0.01) seconds, a substantially diffraction-limited IR image of said at least portion of the given device on detector means that comprise a multiplicity of IR-sensitive regions.

Another exemplary embodiment involves a multistep process that comprises forming an IR image substantially as described, comparing the temperature corresponding to at least one feature of said image to a target value, also substantially as described, and changing, if indicated by the result of the comparing step, at least one of the preceding steps of the process so as to reduce, in a given subsequently produced otherwise identical device, the difference between said temperature and the target value. Exemplarily, the preceding step comprises solder bonding the device to a submount.

Although the invention can be ,used to manufacture a wide variety of semiconductor devices, the method is most advantageously used in the manufacture of devices that are likely to experience considerable thermal stress during normal operation. Among such devices are integrated circuits, microprocessors and microwave devices, and also semiconductor lasers, especially high power lasers of the type used, for instance, to pump optical fiber amplifiers.

DETAILED DESCRIPTION OF AN EXEMPLARY EMBODIMENT

Figure 1:
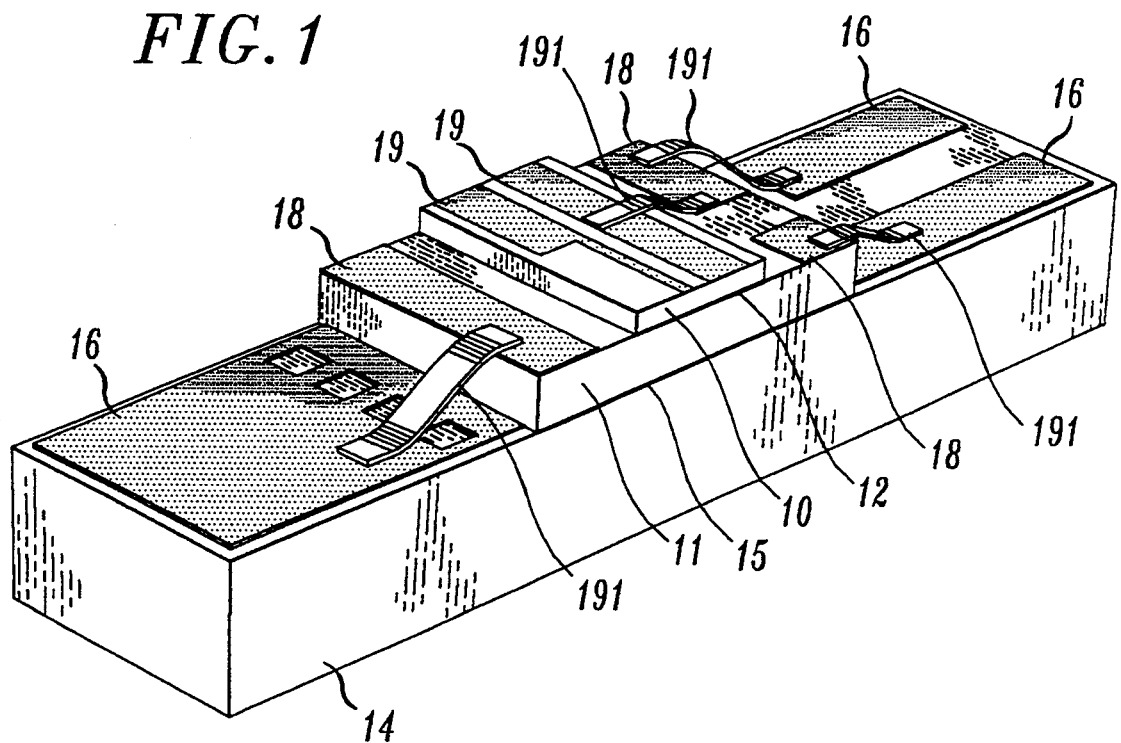
FIG. 1 schematically depicts an exemplary mounted semiconductor laser.

I have recognized that IR imaging apparatus, in order to be more useful for semiconductor device development and/or manufacture, needs to have greatly improved capabilities, as compared to prior art apparatus. Among the required improved capabilities are improved spatial resolution and improved acquisition time. Improved thermal resolution is desirable.

As those skilled in the art know, the spatial resolution of any imaging system is a function of the wavelength that is imaged, and can typically not be less than the wavelength, due to unavoidable diffraction effects. An optical imaging system capable of spatial resolution substantially equal to the theoretical resolution limit is generally referred to as "diffraction limited". Herein the term will refer to a system that is capable of resolving spatial detail of size substantially equal to the longest wavelength in the band of wavelengths to which the system is responsive. Exemplarily, a system that responds to radiation in the 3-5 $\mu$m range is diffraction limited if it is capable of resolving spatial detail of size substantially equal to 5 $\mu$m.

The need for substantially improved spatial resolution arises from the unexpected discovery that, at least in semiconductor lasers, many thermal features of technological significance have spatial extent substantially below the resolution limit of prior art imaging apparatus. The need for substantially shorter acquisition time arises from the finding that real-time imaging of non-stationary thermal states can provide information of significant technological importance, e.g., migration of non-radiative defects.

The invention will now be further described with reference to a particular embodiment, namely, the manufacture of heterostructure lasers for use as pump sources for Er-doped fiber amplifiers.. The lasers were designed to emit at 0.98 $\mu$m or 1.48 $\mu$m, and were of known design. See, for instance, W. B. Joyce et at., *Journal of Applied Physics*, Vol 46(2), p. 855, for a generalized treatment. Techniques for making such lasers are also known.

In view of the typically high operating currents of the exemplary lasers, it is important that the lasers have low thermal impedance between the buried stripe structure and the submount, high resistance in the current blocking regions around the mesa, low and stable electrical resistance in the metal contacts, and a proper solder bond with a good heat sink to prevent excessive heating. I have found that failure to meet any of the above recited device characteristics in a device can lead to localized heating (or possibly excessively high overall temperature) in an energized device. Furthermore, the presence of material defects can facilitate re-combination of carders, resulting in localized heating and activation of point defect motion, the former resulting in dark-line defect formation and the latter frequently leading to catastrophic degradation. Since most of the degradation processes in semiconductor devices are thermally activated, localized heating (or excessive overall temperature) in an energized semiconductor device typically signals the beginning of a degradation process.

I have found that appropriate real-time thermal imaging with high (typically diffraction-limited) spatial resolution of energized devices can advantageously be used to detect anomalous thermal conditions. Thus, such imaging can exemplarily be used to pre-screen potentially unreliable devices by monitoring the deviation of their thermal image from a pre-determined "normal" image, potentially resulting in considerable cost saving. Such imaging can also be used to monitor the quality of a manufacturing process (e.g., the quality of the bonding process that attaches a laser to its heat sink), again potentially resulting in substantial cost saving.

FIG. 1 schematically depicts an exemplary mounted heterostructure laser. Numeral 10 refers to the laser chip (e.g., a InP-based laser, bonded p-side down), 11 to the laser submount, 12 to the solder joint between laser chip and submount, 14 to the heat sink or "stud" (typically a copper block), and 15 to the solder joint between submount and stud. Numerals 16 and 18 refer to bonding pads, 19 to n-side contacts and 191 to conductors (e.g., Au ribbons).

Figure 2:
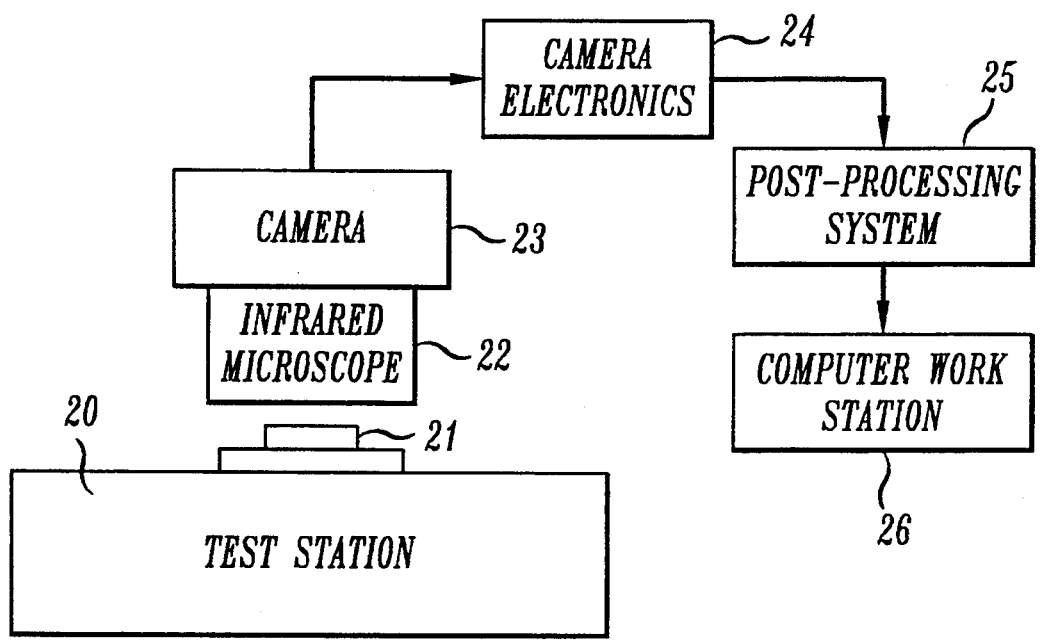
FIG. 2 schematically shows apparatus that can be used in the practice of the invention.

FIG. 2 schematically shows apparatus that can be used in the practice of the invention. Sample 21 (e.g., a semiconductor laser on a heat sink) is positioned on test station 20. The test station comprises conventional means for laser control and cooling. Microscope 22 is focused on the laser surface and forms an IR image on focal plane array camera 23. Optional camera electronics 24 performs A/D conversion on the electrical signal from the camera in known manner, and provides the resulting digital signal to optional real time post-processing system 25 which is provided to perform in known manner a variety of optional mathematical processing on the digital signal from the camera electronics. Exemplary, a commercially available Datacube Max 20 system can be used. Optional computer work station 26 (e.g. commercially available from Sun Microsystems) is used for image analysis and data storage.

The camera was a 128×128 pixel InSb focal plane array camera obtained from Amber Engineering of Santa Barbara, Calif. The camera electronics were designed to provide for, e.g., frame averaging, real-time low pass filtering, Laplacian transformation. These optional capabilities can be obtained with known components, obtainable, for instance, from Datacube, Inc., of Peabody, Mass.

An important component of the IR imaging system is the substantially diffraction-limited optical system, also referred to as the IR microscope. As will be appreciated by those skilled in the art, the optical elements of the microscope have to be substantially transparent at the wavelengths of interest, e.g., 3-5 $\mu$m. For the exemplary wavelength range the optical elements typically consist of geranium and/or silicon.

The microscope desirably provides magnification, typically at least 5x (preferably about 10x), and be "fast", i.e., have a low (<f/4, preferably ≤f/3) f-number. The former inter alia ensures that the image is projected onto a significant portion of the focal plane array, comprising many pixels, and the latter ensures sufficient brightness to yield the desired short acquisition time. The microscope desirably also has a relatively large (e.g., >50 $\mu$m diameter at maximum magnification)

object field, in order for the system to be able to image at least a significant portion of a given semiconductor device or assembly.

Preferred embodiments of the microscope have a relatively large depth of field ($\gtrsim 100$ μm, preferably >300 μm), to facilitate focusing and imaging of non-planar surfaces. In the currently preferred embodiment of the invention the working distance (object distance Do) is 0.5 inch (~12.7 mm), but this is not a requirement, and much larger working distances (e.g., 1 m) may at times be deskable. Due, for instance, to the need for heat shielding, it is typically deskable that the image distance (D i) be relatively large, e.g., greater than 50 mm, exemplarily 100 mm. It is also deskable that the microscope have a low magnification (e.g., 1x-2x) position, in addition to the high magnification position.

As those skilled in the art will appreciate, a unitary (typically multi-element) optical system that meets the above discussed requirements can be designed by application of known principles of lens ,design. However, I have found that all the above requirements can also be met by a microscope that combines two, commercially available, optical components. The first of these is a Si-Ge multi-element component, designated a "1 mil lens", available from FLIR Systems, Inc., of Portland, Oreg. The second component is a f/3 Ge "triplet", suitable for use in conjunction with a 7×7 mm focal plane array, available, for instance, from Diversified Optical Products, Inc., of Salem, N.H. The two components were combined to yield a (3-5 μm) IR microscope having 9x magnification (also having a 1.5x position), about 330 μm depth of field, f/3, 100 mm image distance, 5.6° field of view, 90 μm diameter object field, and 50 mm diameter exit pupil. The microscope was diffraction limited, capable of about 5 μm resolution, and capable of supporting acquisition times much lower than 0.1 (or even 0.01) seconds. Indeed, the exemplary apparatus was capable of acquisition rates up to 217 frames/second, with optional upgrade to 1000 frames/second possible. It had noise equivalent difference temperature (NEAT) of 0.01° C., which was reduced to 0.002° C. at 20° C. when the acquisition system was run in frame averaging mode.

It will be appreciated that the above described instrumentation is exemplary only and, utilizing the disclosures contained herein, those skilled in the art will be able to design and provide other suitable instrumentation.

The thermal images disclosed herein are, for obvious reasons, in black and white. However, as those skilled in the art will have discerned already, images can be readily and advantageously presented in false color. Techniques for accomplishing this are well known.

Figure 3:
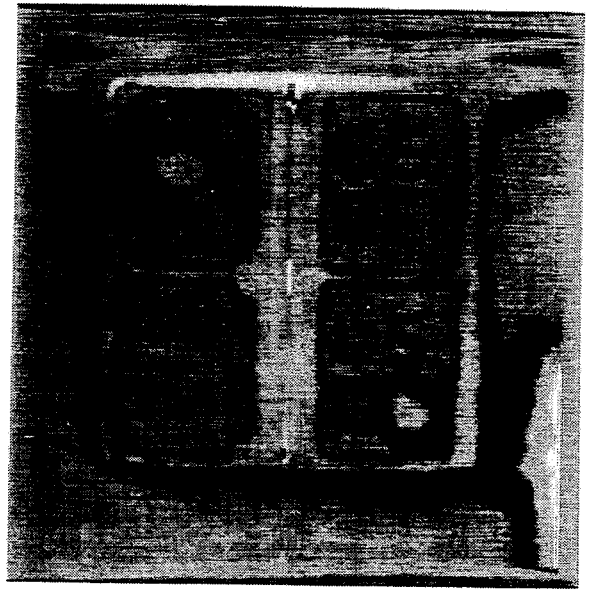
FIGS. 3 and 4 are thermal images of exemplary lasers, viewed from above and from the front, respectively.

FIG. 3 is a black and white reproduction of a top view false color IR image (10x magnification) of a powered semiconductor laser of known design, emitting at 0.98 μm wavelength. The cavity length of the laser is 500 μm. The IR image reveals several regions of elevated temperature (light contrast), including several hot spots in the laser stripe. These hot spots are associated with dark line defects and would detrimentally affect laser lifetime.

Figure 4:
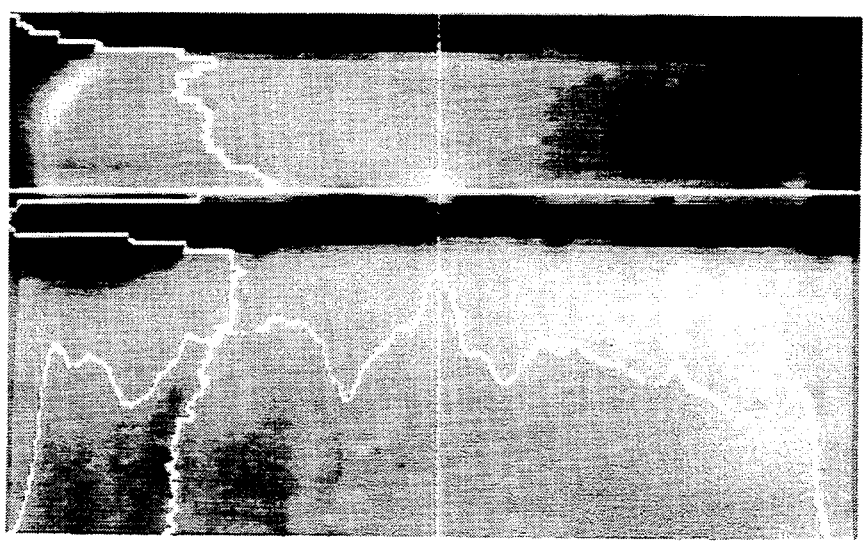

FIG. 4 is a reproduction of a black and white IR image, face on, of a powered laser of known design, emitting at 1.48 μm, solder bonded to a CVD diamond submount. The front facet of the laser has dimensions 500×90 μm. Superimposed on the image are two temperature profiles taken along two traces marked by white lines that intersect in the emission region of the laser. The temperature profiles were derived, essentially in real time, from the IR image as provided by the focal plane array camera. FIG. 4 reveals a small (about 10 μm full width at half maximum) hot spot at the emitting region of the front facet.

I claim:

1. Manufacturing method comprising a multiplicity of manufacturing steps including providing a semiconductor body and forming on and/or in said body one or more semiconductor devices, a given device of said devices having a surface and comprising contact means such that an electrical current can be caused to flow through the given device, the method further comprising causing the flow of electrical current through at least said given device prior to completion of the given device, the given device prior to its completion to be referred to as a given "partially completed" device, the method still further comprising forming an image of at least a portion of said given partially completed device, said image being an infrared image comprising features representative of the temperature at a multiplicity of points of the given partially completed device; comparing the temperature corresponding to at least one of said features of the infrared image to a predetermined target value; and carrying out at least one further step on said one or more devices in accordance with the result of the comparing step;

CHARACTERIZED IN THAT the surface of said given partially completed device is not contacted with liquid during said forming an image; and the method comprises forming the infrared image with imaging apparatus that is adapted for forming, with an acquisition time of no more than 0.1 seconds, a substantially diffraction-limited infrared image of said at least portion of the given partially completed device on detection means that comprise a multiplicity of infrared-sensitive regions.

2. Method according to claim 1, wherein said image is formed with apparatus that comprises optical means (to be referred to as a "microscope") adapted for forming a substantially diffraction-limited magnified infrared image of said at least portion of said device on said detection means, said detection means comprising a focal plane infrared detector array.

3. Method according to claim 2, wherein said detector array is responsive to infrared radiation in the wavelength region 3-5 μm, and said image has a resolution of at least about 5 μm.

4. Method according to claim 2, wherein said optical means are adapted for providing magnification in excess of x5, have depth of focus greater than 100 μm, have an f-number of f/4 or less, wherein said acquisition time is at most 0.01 s, and wherein said image has temperature resolution of 0.01° C. or better.

5. Method according to claim 1, wherein said semiconductor device is an opto-electronic device.

6. Method according to claim 5, wherein said opto-electronic device is a laser.

7. Manufacturing method comprising-providing a semiconductor body and forming, in a multi-step process, on and/or in said body one or more semiconductor devices, a given device of said devices having a surface and comprising contact means such that an electrical current can be caused to flow through the given device, the method further comprising causing the flow of electrical current through at least said given device, forming an image of at least a portion of said given device, said image being an infrared image comprising features representative of the temperatures at a multiplicity of points of the given device, comparing the temperature corresponding to a least one of said features of the image to a predetermined target value, and changing, if indicated by the result of the comparison, at least one of the steps of said multi-step process so as to reduce, in a given subsequently produced otherwise identical semiconductor device, the difference between the temperature corresponding to said feature of the infrared image and the target value;

CHARACTERIZED IN THAT the surface of said given partially completed device is not contacted with liquid during said forming an image; and the method comprises forming the infrared image with imaging apparatus that is adapted for forming, with an acquisition time of no more than 0.1 seconds, a substantially diffraction-limited infrared image of said at least portion of the given device on detector means that comprise a multiplicity of infrared-sensitive regions.

* * * * *

UNITED STATES PATENT AND TRADEMARK OFFICE
CERTIFICATE OF CORRECTION

PATENT NO.  : 5,396,068

DATED       : March 7, 1995

INVENTOR(S) : Clyde George Bethea

It is certified that an error appears in the above-identified patent and that said Letter is hereby corrected as shown below:

```
     Column 6, line 40 "(to" should be deleted.  Column 6,
line 41 "be-referred to as a "microscope")"  should be deleted.
Column 6, line 60 "comprising-providing" should read --comprising
providing--.
```

Signed and Sealed this

Twenty-seventh Day of June, 1995

Attest:

BRUCE LEHMAN

*Attesting Officer*    *Commissioner of Patents and Trademarks*